(12) United States Patent
Carrano et al.

(10) Patent No.: US 9,475,042 B2
(45) Date of Patent: *Oct. 25, 2016

(54) SPECIMEN DELIVERY APPARATUS

(71) Applicant: Paratus Diagnostics, LLC, Austin, TX (US)

(72) Inventors: John C. Carrano, Austin, TX (US); Roland Schneider, Austin, TX (US); John J. Carrano, Austin, TX (US)

(73) Assignee: Paratus Diagnostics, LLC, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/920,516

(22) Filed: Oct. 22, 2015

(65) Prior Publication Data

US 2016/0038933 A1  Feb. 11, 2016

Related U.S. Application Data

(63) Continuation of application No. 13/918,877, filed on Jun. 14, 2013.

(60) Provisional application No. 61/659,431, filed on Jun. 14, 2012.

(51) Int. Cl.
*B01L 3/00* (2006.01)
*G01N 1/38* (2006.01)

(52) U.S. Cl.
CPC ............ *B01L 3/502* (2013.01); *B01L 2200/06* (2013.01); *B01L 2200/10* (2013.01); *B01L 2200/16* (2013.01); *B01L 2300/041* (2013.01); *B01L 2300/046* (2013.01); *B01L 2300/0636* (2013.01); *B01L 2300/087* (2013.01); *B01L 2300/0867* (2013.01); *B01L 2300/123* (2013.01); *B01L 2400/0481* (2013.01); *B01L 2400/0683* (2013.01); *G01N 1/38* (2013.01)

(58) Field of Classification Search
CPC .... B01L 3/502; B01L 3/565; B01L 2300/10; B01L 2300/41; B01L 2300/46; B01L 2300/861; B01L 2300/123
See application file for complete search history.

(56) References Cited

U.S. PATENT DOCUMENTS

| 4,753,775 A * | 6/1988 | Ebersole ................ B01L 3/021 422/400 |
| 5,863,502 A * | 1/1999 | Southgate ............ B01J 19/0046 422/417 |
| 6,432,720 B2 * | 8/2002 | Chow ...................... 204/403.14 |
| 6,645,758 B1 * | 11/2003 | Schnipelsky ........... B01L 3/502 422/547 |
| 8,318,439 B2 * | 11/2012 | Battrell ............. B01L 3/502776 424/93.7 |
| 8,506,908 B2 * | 8/2013 | Benn ................ G01N 35/00029 204/400 |

(Continued)

*Primary Examiner* — Brian R Gordon
(74) *Attorney, Agent, or Firm* — McGuireWoods, LLP

(57) ABSTRACT

A specimen delivery apparatus includes a housing having a backplane. The backplane includes at least one fluid communication port. The housing has an open state and a closed state. A midplane has a cavity for holding a sample. The midplane is sealed within the housing when the housing is in the closed state. A first actuator is disposed to move fluid within the housing when the housing is in a closed state and the first bulb is actuated. Various embodiments provide for caching of the fluid as well as staging to permit further preparation of the specimen prior to delivery. Various features roil the fluid to assist in extraction, mixing, and transport of the sample with the fluid. A destructible seal prevents fluid communication through the fluid communication port while the seal is intact. Communication of fluid through the fluid communication port is enabled only when the destructible seal is not intact.

26 Claims, 14 Drawing Sheets

(56) References Cited

U.S. PATENT DOCUMENTS

| | | | |
|---|---|---|---|
| 9,085,745 B2* | 7/2015 | Eckelberry | C11B 3/005 |
| 2010/0120083 A1* | 5/2010 | Ritzen | B01L 3/502715 |
| | | | 435/30 |
| 2012/0164627 A1* | 6/2012 | Battrell | B01F 11/0071 |
| | | | 435/5 |
| 2013/0142708 A1* | 6/2013 | Battrell | B01L 3/502776 |
| | | | 422/430 |
| 2013/0302787 A1* | 11/2013 | Agarwal | C12N 15/1006 |
| | | | 435/5 |
| 2013/0337432 A1* | 12/2013 | Cook | G01N 21/66 |
| | | | 435/2 |
| 2014/0072474 A1* | 3/2014 | Kido | B01F 11/0074 |
| | | | 422/82.09 |

\* cited by examiner

SPECIMEN DELIVERY APPARATUS

CROSS-REFERENCE TO RELATED APPLICATIONS

This application is a continuation of U.S. patent application Ser. No. 13/918,877 filed on Jun. 14, 2013 entitled SPECIMEN DELIVERY APPARATUS, which claims the benefit of provisional patent application No. 61/659,431, filed Jun. 14, 2012 both of which are incorporated herein by reference.

TECHNICAL FIELD

This invention relates to the field of medical diagnostics. In particular, this invention is drawn to a specimen delivery apparatus for in vitro medical diagnostic devices including point-of-care in vitro medical diagnostic devices.

SUMMARY

A specimen delivery apparatus includes a housing having a backplane. The backplane includes at least one fluid communication port. The housing has an open state and a closed state. A midplane has a cavity for holding a sample. The midplane is sealed within the housing when the housing is in the closed state. A first bulb is disposed to move fluid within the housing when the housing is in a closed state and the first bulb is actuated. A destructible seal prevents fluid communication through the fluid communication port while the seal is intact. Actuation of the first bulb communicates fluid through the fluid communication port when the destructible seal is not intact.

Another embodiment of a specimen delivery apparatus includes a housing having a backplane. The backplane includes at least one fluid communication port. The housing has an open state and a closed state. A midplane has a cavity for holding a sample. The midplane is sealed within the housing when the housing is in the closed state. The apparatus includes a cache. A first actuator is disposed to move fluid within the apparatus when the housing is in a closed state and the first actuator is actuated. A portion of the fluid is cached by the cache upon actuation of the first actuator. A destructible seal prevents fluid communication through the fluid communication port while the seal is intact. Actuation of the first actuator communicates fluid other than the cached fluid through the fluid communication port when the destructible seal is not intact.

Another embodiment of a specimen delivery apparatus includes a housing having a backplane. The backplane includes at least one fluid communication port. The housing has an open state and a closed state. A midplane has a cavity for holding a sample. The midplane is sealed within the housing when the housing is in the closed state. A first bulb is disposed to move fluid within the apparatus when the housing is in a closed state and the first bulb is actuated. A latching apparatus co-operates with the housing to retain the first bulb in a compressed state when the first bulb is actuated. A destructible seal prevents fluid communication through the fluid communication port while the seal is intact. Actuation of the first bulb communicates fluid through the fluid communication port when the destructible seal is not intact.

Another embodiment of a specimen delivery apparatus includes a housing having a backplane. The backplane includes at least one fluid communication port. The housing has an open state and a closed state. A midplane has a cavity for holding a sample. The midplane is sealed within the housing when the housing is in the closed state. A fluid transport path includes features to roil fluid propelled through the fluid transport path. A first actuator is disposed to move fluid within the apparatus through at least a portion of the fluid transport path when the housing is in a closed state and the first actuator is actuated.

Another embodiment of a specimen delivery apparatus includes a housing having a backplane. The backplane includes at least one fluid communication port. The housing has an open state and a closed state. A midplane has a cavity for holding a sample. The midplane is sealed within the housing when the housing is in the closed state. The apparatus includes a staging chamber. A first actuator transports fluid within the apparatus to the staging chamber when the housing is in a closed state and the first actuator is actuated. A destructible seal preventing fluid communication through the fluid communication port while the seal is intact. Actuation of a second actuator transports fluid from the staging chamber through the fluid communication port when the destructible seal is not intact.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which.

DETAILED DESCRIPTION

One approach to diagnosing medical ailments often entails steps such as collecting a sample from a patient, preparing a specimen from the sample, analyzing the specimen to assay the presence of various biological or chemical analytes, and interpreting the presence and amount of the analytes or their absence to derive a diagnosis. The study of samples of tissues and bodily fluids outside of the body is referred to as in vitro analysis.

Figure 1:
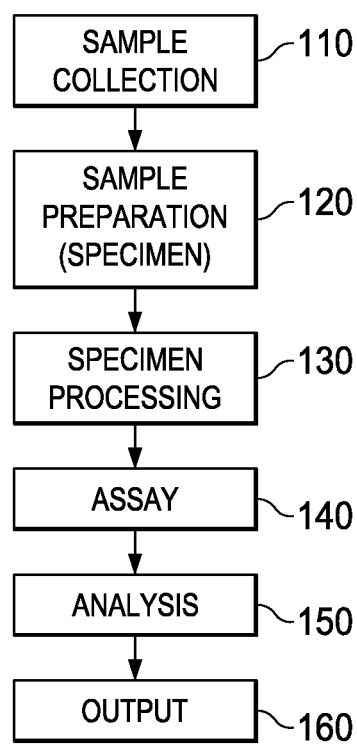
FIG. 1 illustrates an embodiment of a functional block diagram for performing a medical diagnosis.

FIG. 1 illustrates one embodiment of a process for performing an in vitro medical diagnosis. A sample of the tissue, fluid, or other bodily matter is collected in step 110. The sample is typically prepared in order to form a specimen in step 120. Preparation of the sample might include, for example, elution, mixing, or lysing in order to produce a specimen. In some cases, the sample serves as a specimen as collected. Further specimen processing may be performed at step 130.

After specimen processing, an assay is performed in step 140. In vitro analysis examines specimens for biological or chemical components. The assay may be qualitative, quantitative, or both. An analysis of the assay results is performed in step 150. The result of the analysis is then output in step 160.

The sample is collected from the patient at the point of care. The remaining steps may be performed on- or off-site or in any combination thereof. For example, samples or specimens may be sent to offsite laboratories with sophisticated equipment and highly trained laboratory personnel that process the specimen for analysis. To the extent these functions can be incorporated into a point-of-care medical diagnostic system, the cost and length of time required for diagnosing an ailment may be reduced considerably. The lead time for treatment as well as the cost for treatment may likewise be reduced. The medical diagnostic device may also indirectly protect populations other than the patient, particularly when dealing with detecting contagious diseases and assessing aggregate data for timely determining the onset or scope of an epidemic. Point-of-care medical diagnostic devices can offer significant healthcare benefits.

With respect to incorporating the process of FIG. 1 into a point-of-care medical diagnostic system, the functional blocks may be distributed across a number of components in order to enable economically efficient and practice efficient in vitro medical diagnostic devices.

Figures 2A, 2B:
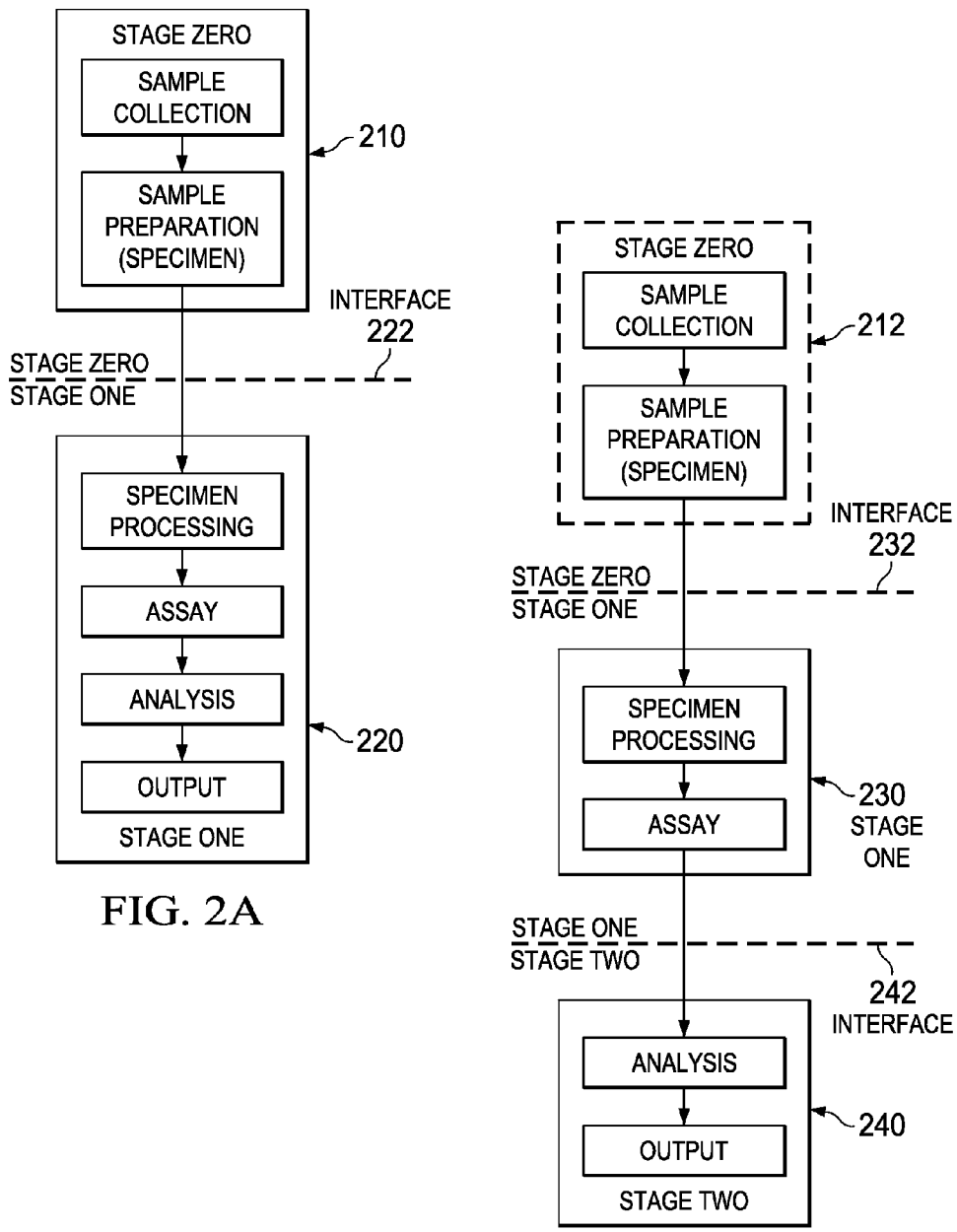
FIGS. 2A and 2B illustrate embodiments of a modular staged point-of-care medical diagnostic system.

Referring to FIG. 2, for example, in one embodiment of an in vitro medical diagnostic system, the functional blocks including sample acquisition and sample preparation are incorporated into stage zero component 210. Functional blocks including specimen processing, assay, analysis, and output are incorporated into one or more components.

In one embodiment, functional blocks including specimen processing and assay are incorporated into a stage one component 230. Functional blocks for analysis and output are incorporated into another component, stage two component 240. In an alternative embodiment, specimen processing, assay, analysis, and output are incorporated into a single component, the stage one component 220.

The distribution among various components enables staging of the medical diagnostic system to facilitate both practice and economic efficiency. Any component directly handling specimens will either have to be disposed of or alternatively sterilized before re-use.

In one embodiment, stages zero and one are disposable components. The analysis function is generally a computational function. If cost or practice efficient to do so, the analysis function may be incorporated into a disposable component. In one embodiment, however, the analysis function is incorporated into a subsequent stage ("stage two") that need not be disposed of Modular staging enables the greatest flexibility to allocate diagnostic functions between components to realize practice and cost efficiencies.

The stages interface with a person or each other at various interfaces. In a point-of-care medical diagnostic system, physical coupling between stage one and any subsequent stage likely only needs to support electrical or optical signals. The electrical and signaling interface between stage one and any subsequent stage may be proprietary. Training requirements for coupling such stages together is minimal. Thus, for example, the stage one/stage two interface 242 might consist simply of an electrical connector.

The stage zero/stage one interface 222, 232 is likewise designed for ministerial level skills. Although different versions of specimen delivery systems (stage zero) might be necessary due to accommodate different types of samples or different specimen preparation processes, for example, the use of a standardized interface such as a snap-in or plug-in type of coupling ensures that only ministerial skill levels are needed to couple the specimen delivery apparatus to the next modular stage of the point-of-care medical diagnostic system.

In contrast, the interface between the patient and stage one may be indirect and involve a number of steps that previously required significant skills or training and equipment. Acquisition of typical samples from a patient is largely a mechanical task and does not require significant training. Typical samples, for example, consist of fluids or tissue. Collection of these samples is performed by a clinician or provided by the patient using standard clinical techniques (e.g., blood, dried blood, urine, sputum, mucous, etc.).

Sample preparation can impose much greater training requirements. Sample preparation might be performed by a laboratorian and is susceptible to variations in user experience, skill set, and preparation environmental conditions. In addition, sample preparation often required additional equipment for measuring and mixing along with a separate inventory of the items that the sample would be mixed with.

A specimen delivery apparatus is proposed to reduce or eliminate the need for skilled practitioners or laboratory personnel. Standard clinical practices for obtaining samples from the patient may be utilized to collect the sample. Although the functions performed by the specimen delivery apparatus might qualify as complex, the function is largely abstracted from the user. In particular, the user performs low-complexity tasks (e.g., select an appropriate specimen delivery apparatus, place the sample in the specimen delivery apparatus, close the selected specimen delivery apparatus, attach the specimen delivery apparatus to a subsequent stage, and actuate a bulb on the specimen delivery apparatus). The specimen delivery apparatus may be configured to support various samples and sample preparation needs.

Figure 3A:
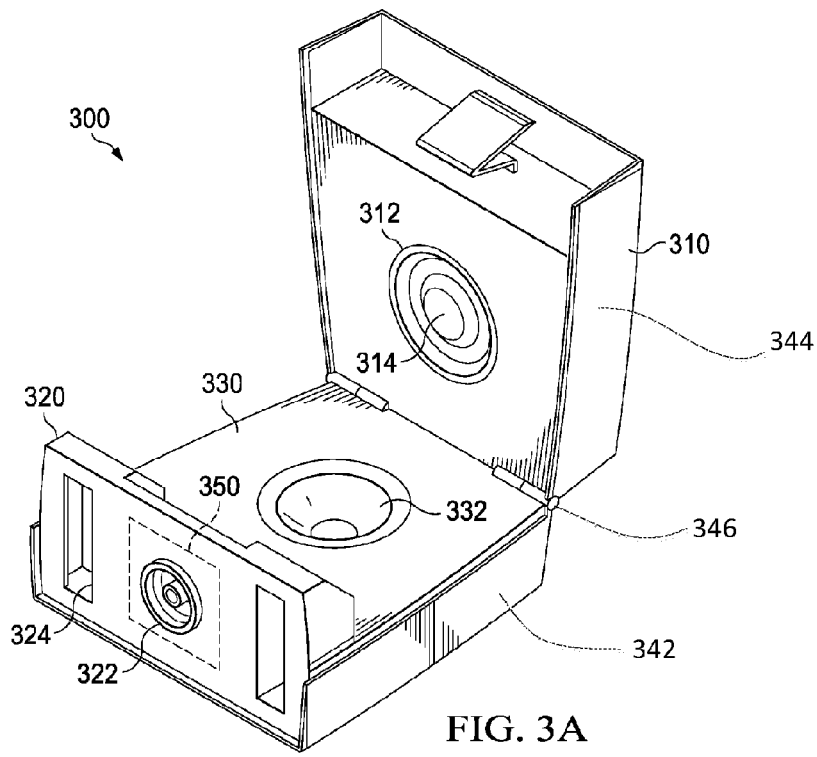
FIGS. 3A-3C illustrate an embodiment of a specimen delivery apparatus.
Figure 3B:
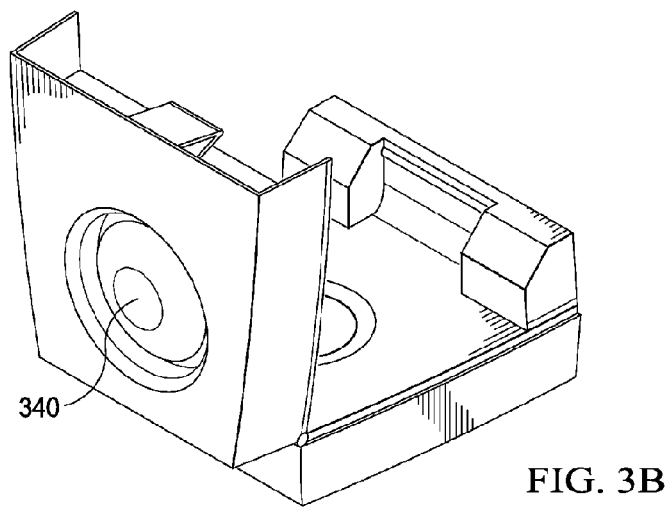
Figure 3C:
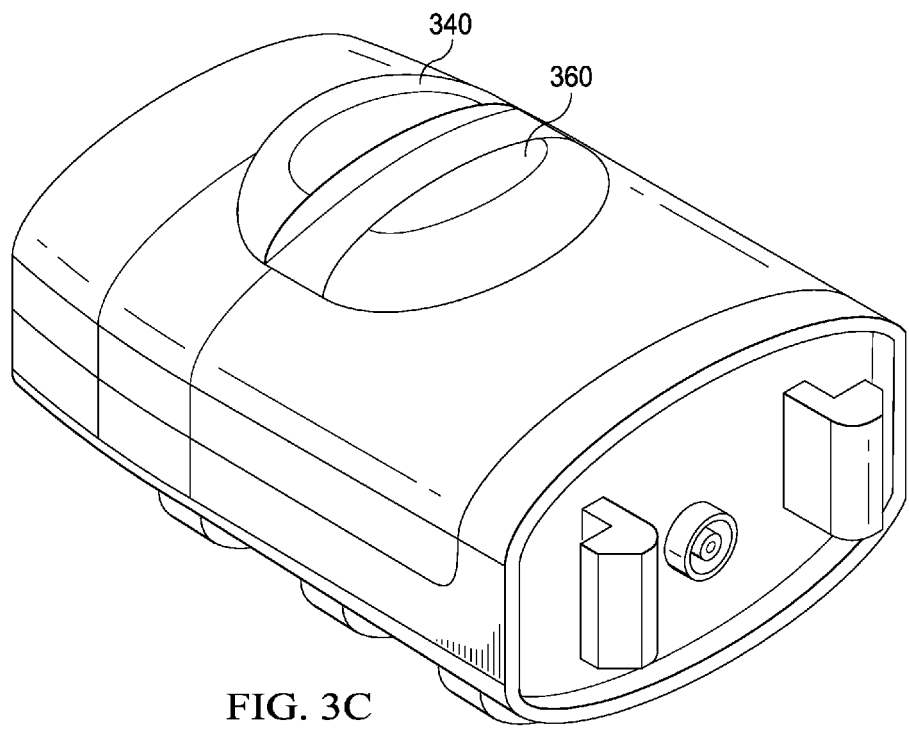

FIGS. 3A-3C illustrate an embodiment of a specimen delivery apparatus 300. The specimen delivery apparatus includes a housing 310 having a first portion 342 and a second portion 344 coupled at a hinge 346. The housing has an open state and a closed state. In one embodiment, the housing is hinged such that the housing may be closed by moving the second portion 344 toward the first portion 342. The housing includes a backplane 320, which includes at least one fluid communication port 322, and may thereby be referenced as an interfacing surface. A midplane 330 serves as intermediate portion having a cavity 332 for holding a sample. The midplane 330 is sealed within and positioned between the first portion 342 and second portion 344 of the housing when the housing 310 is in the closed state.

In one embodiment, the housing includes locking features to secure the housing in a closed state once closed. Thus a sample may be placed in the housing in the open state. Once closed, the features prevent the housing from being opened back up. Such features aid in the containment of medical waste.

A first actuator 340 is disposed to move fluid within the housing when the housing is in the closed state and the first actuator is actuated. In the illustrated embodiment, the first actuator is a bulb and is referred to as first bulb 340. A destructible seal 350 prevents fluid communication through the fluid communication port while the seal is intact. Actuation of the first bulb communicates fluid through the fluid communication port when the destructible seal is not intact.

In one embodiment, the specimen delivery apparatus includes a second actuator or second bulb 360. Alternate actuation of the first and second bulbs moves fluid within the housing when the destructible seal is intact. Actuation of the first or second bulb moves fluid through the fluid communication port when the destructible seal is not intact.

In one embodiment, a "locking" mechanism is employed for one or more bulbs. The locking mechanism maintains the bulb in a depressed position once actuated. One embodiment of the locking mechanism includes a shell covering a flexible portion of the bulb. The shell includes features to latch onto mating features of the housing when depressed. The locking mechanism prevents the specimen delivery apparatus from drawing or siphoning fluid back through the fluid communication port. The locking mechanism also serves to provide visual feedback indicative of a used specimen delivery apparatus. Another advantage of a bulb locking mechanism includes tactile feedback for the user: when the locking mechanism "snaps" into place and retains the bulb, the user may be confident that the user has completed the delivery task.

In one embodiment, the backplane includes at least one attachment point 324 for mechanically coupling the specimen delivery apparatus to a subsequent stage of the point-of-care medical diagnostic system. When coupled via the attachment point, the fluid communication port of the specimen delivery apparatus is aligned with a fluid communication port of the subsequent stage to enable fluid communication between the specimen delivery apparatus and the subsequent stage. In one embodiment, the attachment point includes features to prevent de-coupling of the specimen delivery apparatus and subsequent stage once coupled.

To facilitate sample preparation, the housing includes a blister pack retainer 312. A blister pack 314 containing a sample preparation fluid is placed in the blister pack retainer. In one embodiment, closing the housing causes the blister pack to burst and release its contents. In an alternative embodiment, the first bulb is disposed such that actuation of the first bulb when the housing is closed causes the blister pack to burst and release its contents.

The use of a blister pack substantially eliminates the need to have external laboratory equipment, supplies, or skilled personnel for sample preparation. The blister pack may be selected for the appropriate sample preparation.

In one embodiment, the blister pack contains a fluid for mixing with and carrying the sample in suspended, diluted, or dissolved form. In another embodiment, the blister pack contains a reagent such as a lysing agent to react with the sample. In one embodiment, the blister pack contains an elution buffer. In another embodiment, the blister pack contains an anti-coagulant. In yet another embodiment, the blister pack contains a solvent to enable extraction of the sample from any carrier it has adhered to. For example, a solvent may be appropriate to extract mucous or similar such samples from a swab.

In one embodiment, a fluid transport tube is coupled to carry fluid from the cavity to the fluid communication port. In one embodiment, the fluid transport tube is rifled to enhance mixing of fluids transported from the cavity to the fluid communication port.

Figure 4B:
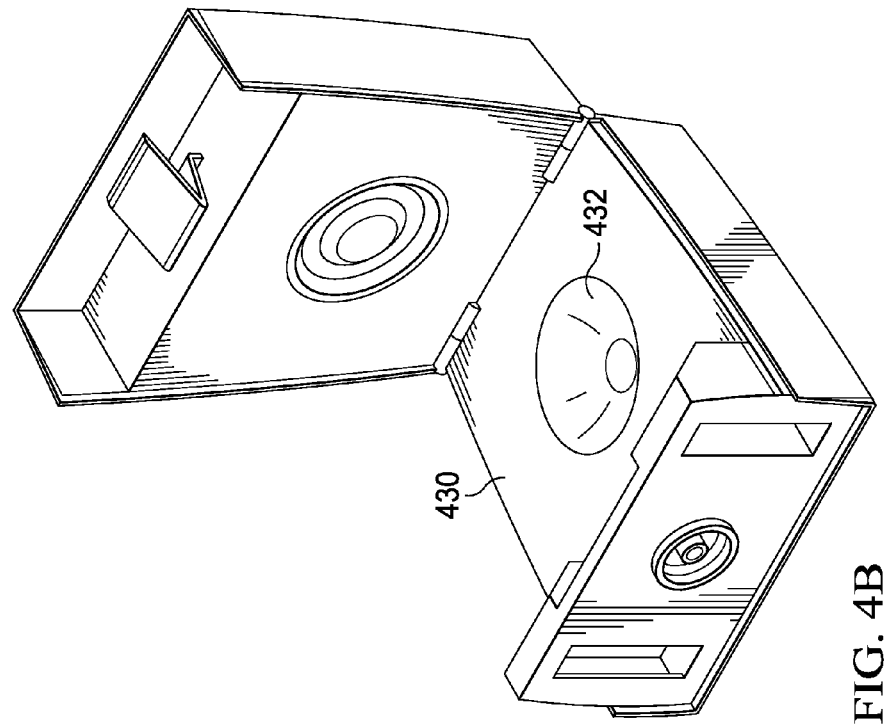
FIGS. 4A-4C illustrate variations on the form factor of the cavity of the specimen delivery apparatus midplane.
Figure 4A:
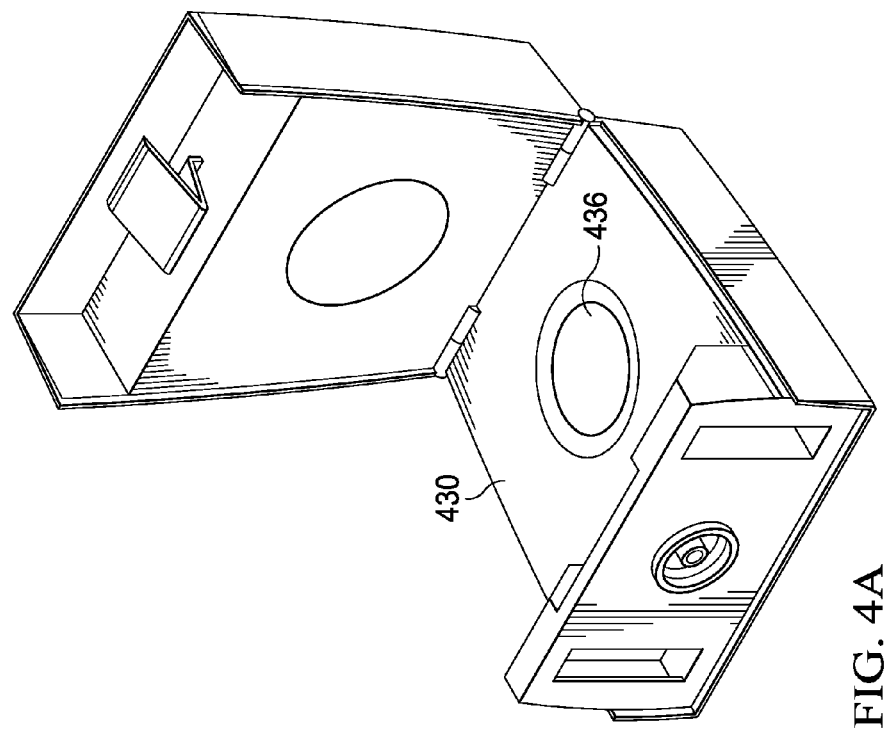
Figure 4C:
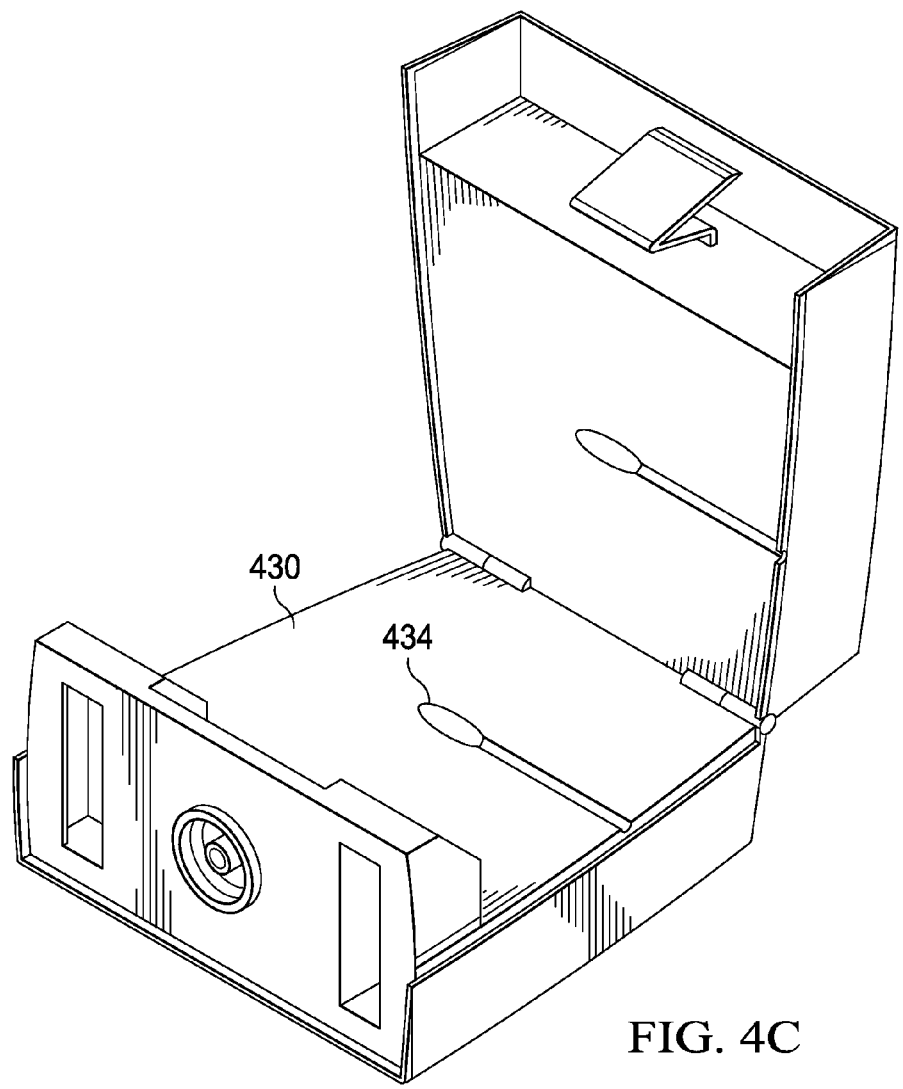

FIGS. 4A-4C illustrate variations on the form factor of the cavity of the midplane 430. The form factor is chosen to facilitate a particular clinical technique or volume associated with the sample being collected. Frequent sample types or sources include blood, urine, tissue, sputum, and mucous.

For example, a hemispheroidal cavity 432 may be appropriate for liquids such as urine or blood. A cavity having a longitudinal cross-sectional profile substantially the same as that of a swab 434 is used for samples collected by and carried by swab. In one embodiment, the midplane has an open cylindrically-shaped cavity 436.

Figure 5:
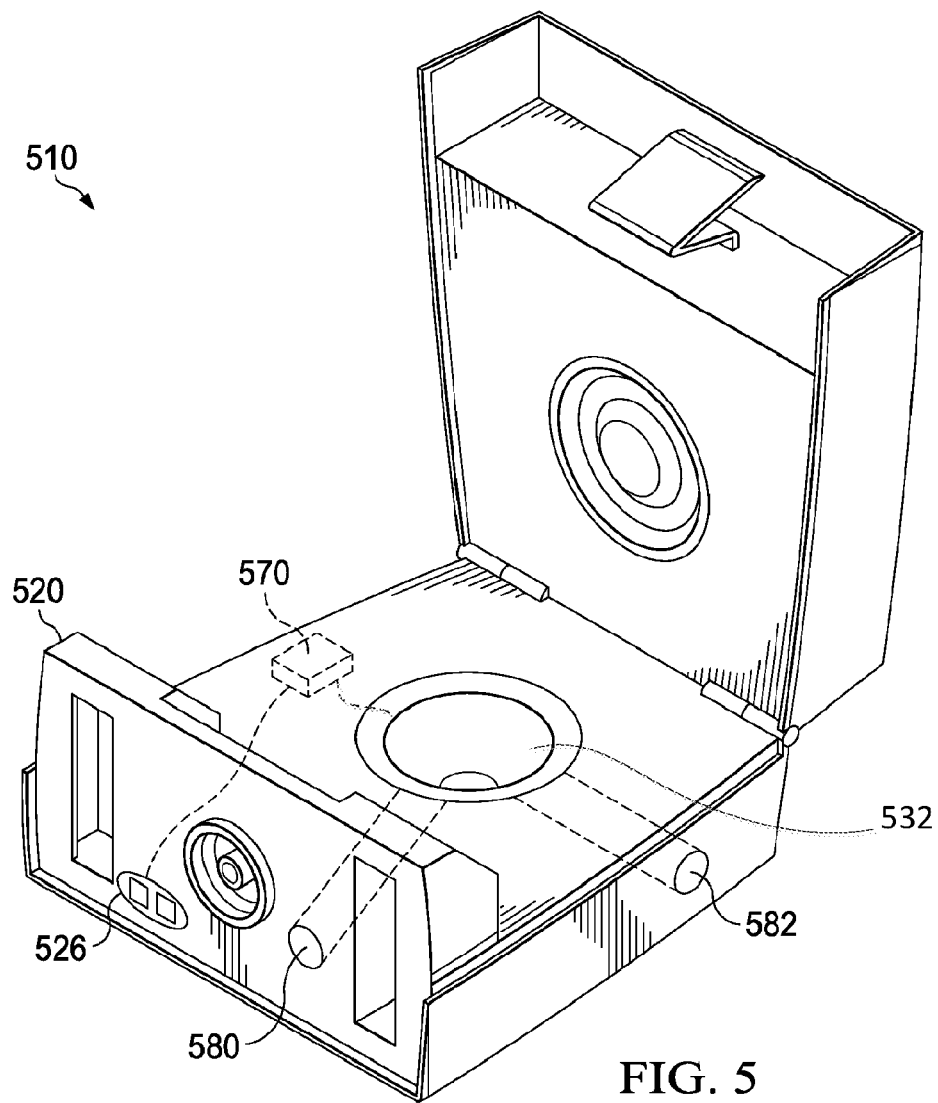
FIG. 5 illustrates another embodiment of the specimen delivery apparatus.

FIG. 5 illustrates another embodiment of the specimen delivery apparatus 510. Backplane 520 includes an electrical port 526 for communication of electrical power to an element 570 within the apparatus. In one embodiment, element 570 is a transducer coupled to the electrical port for applying at least one of a thermal, mechanical, acoustical, or optical energy to the fluid upon application of electrical power to the electrical port.

In one embodiment, the electrical port enables communication of electrical power directly to fluid within the cavity 532 of the apparatus upon application of electrical power to the electrical port. Such a feature may be used to enable lysis via pulsed application of power.

In one embodiment, element 570 is a heater for heating fluid within the apparatus upon application of power to the electrical port. Thermal energy may be used for lysis or sanitization. In one embodiment, element 570 is an acoustic transducer for application of acoustic energy to fluid within the apparatus. Acoustic energy may be used to create cavitation and heat within the fluid sufficient to cause lysis within various biological substances. In one embodiment, the acoustic transducer is a piezoelectric element.

The apparatus may include one or more optical ports 580, 582. In one embodiment, an optical port is included to enable inspection of the contents of the specimen delivery apparatus. In one embodiment, an optical port is included to enable the application of optical energy to the contents of the specimen delivery apparatus.

Figure 6:
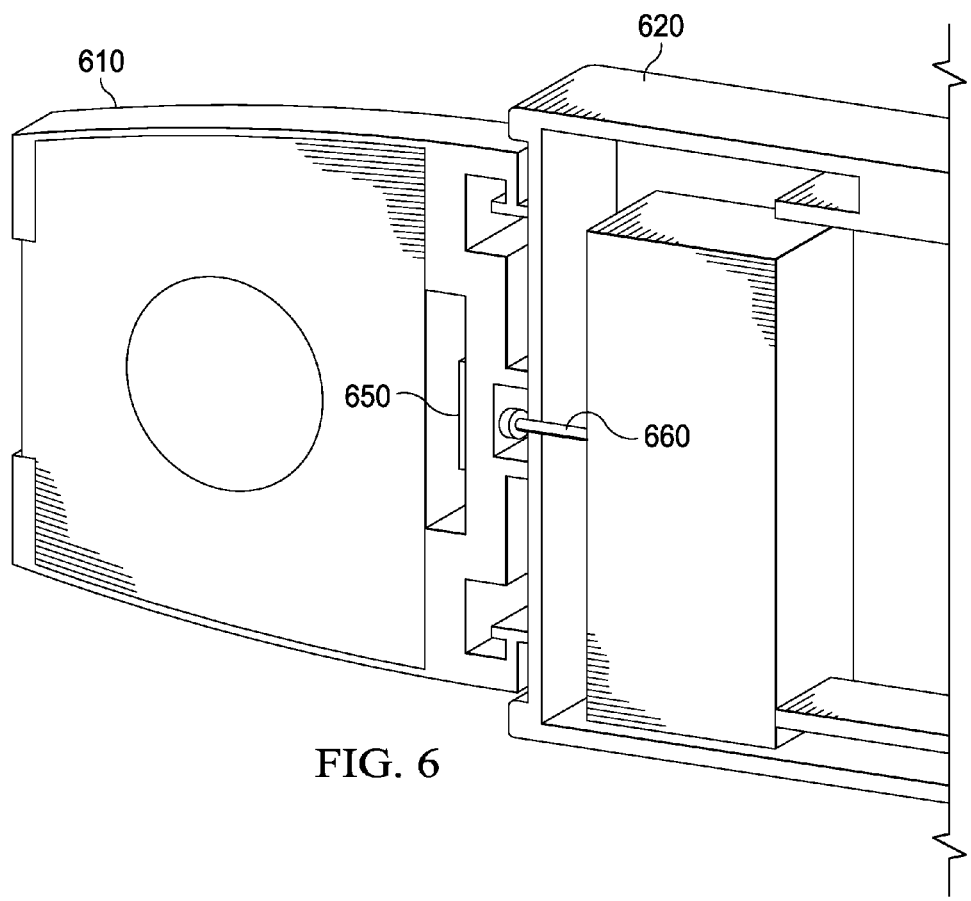
FIG. 6 illustrates attachment of the specimen delivery apparatus to another device.

FIG. 6 illustrates the attachment of the specimen delivery apparatus 610 to the next stage 620 of the point-of-care medical diagnostic system. Upon attachment, the destructible seal 650 is pierced (e.g., by piercing probe 660) such that it is no longer intact. Actuation of a bulb of the specimen delivery apparatus forces fluid communication of the specimen from the specimen delivery apparatus to the next stage of the point-of-care medical diagnostic system.

Figure 7A:
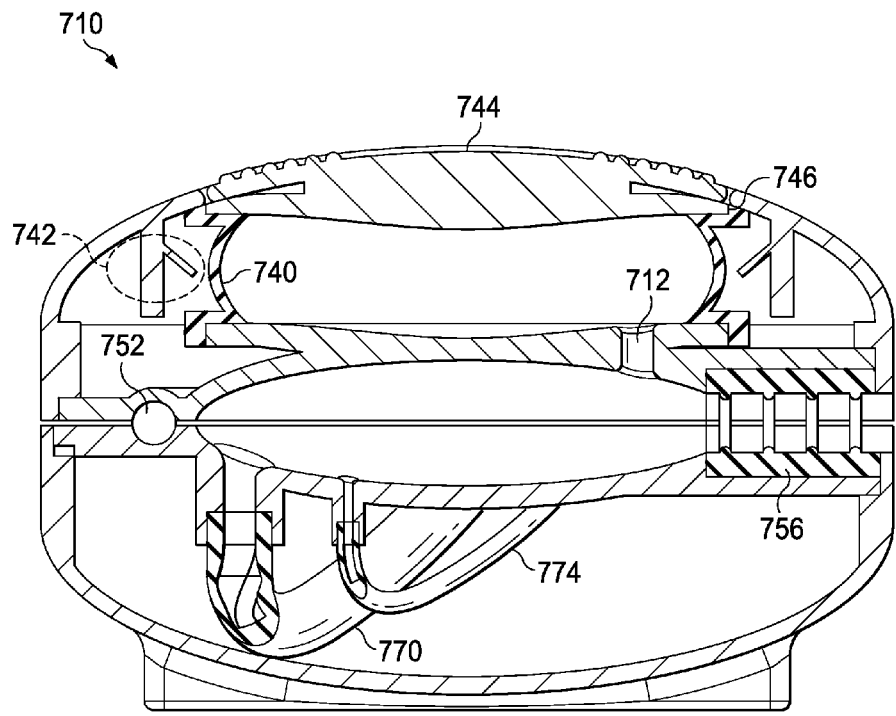
FIGS. 7A and 7B illustrate a cross-section of one embodiment of a specimen delivery apparatus with a bulb locking mechanism
Figure 7B:
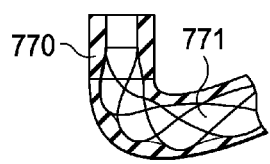

FIGS. 7A and 7B illustrate a cross-section of one embodiment of the specimen delivery apparatus 710 with a bulb locking mechanism. The housing includes retaining apparatus 742 to maintain the bulb 740 in a depressed position once actuated. A shell 744 covers the flexible portion of the bulb.

The shell includes latching features 746 to latch onto or to be retained by the retaining apparatus. The locking mechanism prevents the specimen delivery apparatus from drawing or siphoning fluid back through the fluid communication port. Once the shell is depressed sufficiently to capture or to be captured by the retaining apparatus, the bulb will be maintained in a depressed position. The bulb locking mechanism provides tactile feedback for the user: when the locking mechanism "snaps" into place and retains the bulb, the user may be confident that the user has completed the delivery task. In addition, the locking mechanism provides visual feedback indicative of a used specimen delivery apparatus.

FIG. 7A also illustrates a midplane configured for a swab. One or more seals 752 serve to prevent the sample from escaping the sampling apparatus through unintended routes. In one embodiment, the midplane and housing include features that co-operate to form at least one swab shaft seal 756. The swab shaft seal(s) assist in preventing the sample from escaping along the shaft of the swab.

In one embodiment, rather than using a separate blister pack the bulb 740 may be filled with the fluid to be mixed with the sample. In the illustrated embodiment, the fluid is propelled through tube 712 into the sample chamber that is adapted for a swab.

The fluid transport path transports the fluid to a location internal or external to the specimen delivery apparatus. The fluid transport path may include a portion of the midplane as well as channels, tubes, or intermediate storage mechanisms. The fluid transport path itself may include features to facilitate extracting the sample and mixing the sample with the fluid to prepare and transport the specimen.

For example, the fluid transport path may include channels or fluid transport tube(s) 770, 774 to transport the fluid to a location internal or external to the specimen delivery apparatus. The channel or fluid transport tube(s) may be rifled or have rifling 771 as indicated by the callout for fluid transport tube 770 in order to enhance mixing and transport of the fluid and sample. Features such as the rifling cause the fluid and material carried by the fluid to roil. The roiling effect aids in mixing and transport.

In one embodiment, the specimen delivery apparatus includes a validation cache. The purpose of the cache is to retain a clinically relevant amount of the sample within the housing in order to permit independent testing. Fluid transport tube 770 carries the fluid to a fluid communication port. Fluid transport tube 774 carries fluid to the cache.

Figure 8A:
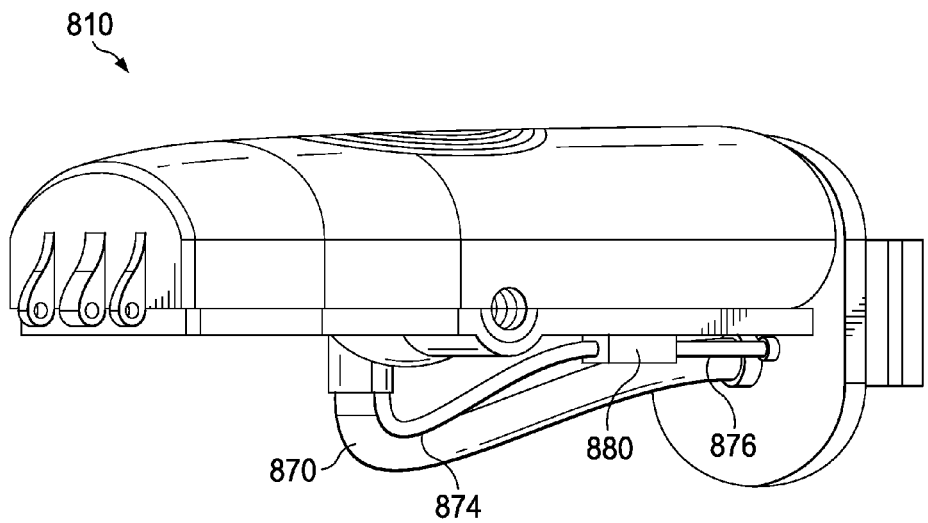
FIGS. 8A and 8B illustrates an embodiment of the specimen delivery apparatus with a validation cache.

FIG. 8A illustrates a side view of a cutaway of one embodiment of the specimen delivery apparatus 810 including a validation cache 880. A fluid transport tube 874 is provided to carry fluid to the cache. In one embodiment another fluid transport tube 876 carries fluid away from the cache. In alternative embodiments, the contents of the cache may be accessed by extraction through other apparatus such as a stopper as found with vials and ampules.

Figure 8B:
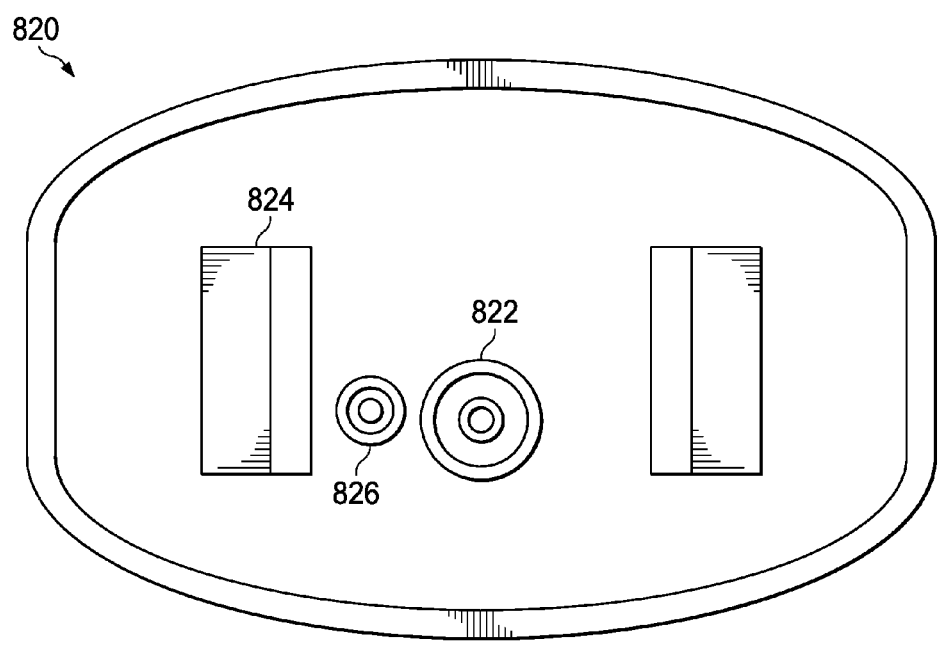

FIG. 8B shows a front view of the backplane 820, and illustrates the primary fluid communication port 822 to be used with next stage point of care. Generally although a fluid transport tube 876 might couple the cache to a cache fluid communication port 826, the next stage device utilizing the primary fluid communication port 822 will not be the same device that utilizes the cache fluid communication port 826. In the field, the attachment points 824 coupling the specimen delivery apparatus to the next stage prevent field separation of the specimen deliver apparatus and the next stage. In one embodiment, a special tool may be utilized to permit separation of the specimen delivery apparatus and the next stage in order for the validation lab to gain access to a cache fluid communication port 826 positioned on the backplane 820.

Figure 9:
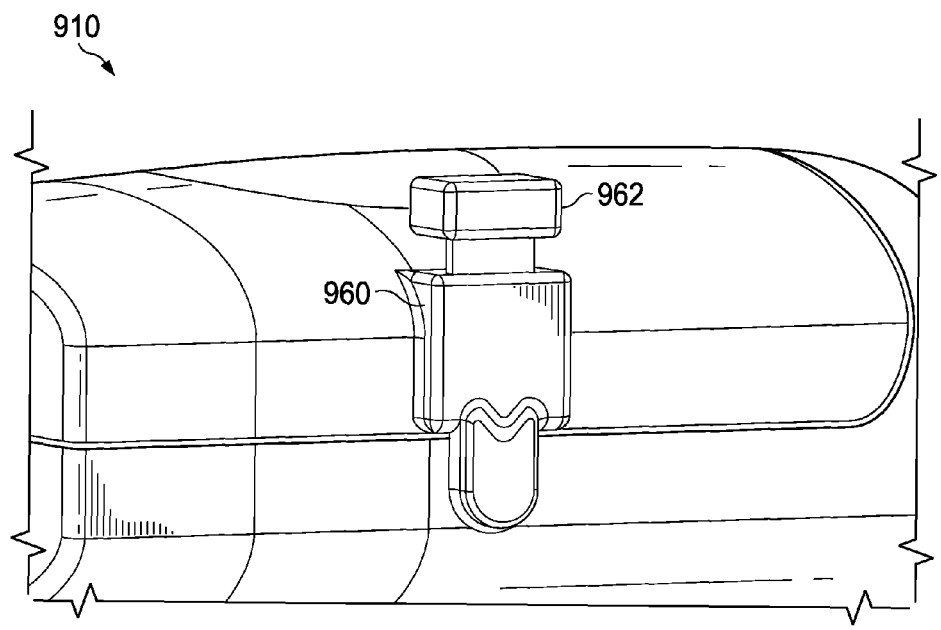
FIG. 9 illustrates an embodiment of a swab cutter for a specimen delivery apparatus.

The shaft portion of a swab is a nuisance once the sample is acquired and placed within the specimen delivery apparatus. A swab may have a pre-scored shaft to facilitate breaking off the shaft after the sample is disposed within the specimen delivery apparatus. Alternatively the specimen delivery apparatus may include a swab cutter to neatly trim away excess swab shaft material. FIG. 9 illustrates one embodiment of a swab cutter 960 for a specimen delivery apparatus 910. The swab cutter includes a blade (not shown) or other cutting apparatus coupled to the button 962. After placement of the swab in the specimen delivery apparatus and closing specimen delivery apparatus, the button 962 of the swab cutter may be depressed to sever the swab shaft.

The fluid transport path may be configured to accomplish goals in addition to transport. As addressed above, channels or fluid transport tubes can include rifling or other features to facilitate transport and mixing. In some cases, the sample may be carried by a tool such as a swab from which the sample must be stripped in order to prepare the specimen. When the specimen delivery apparatus is in the closed position, the swab is held within a chamber formed by the housing and the midplane cavity. In order to extract more sample from the swab, the chamber may include features to create a roiling effect when fluid is driven into the chamber. The chamber forms a portion of the fluid transport path. Thus the fluid transport path may include features to strip or extract, mix, and carry the sample when preparing the specimen.

Figure 10:
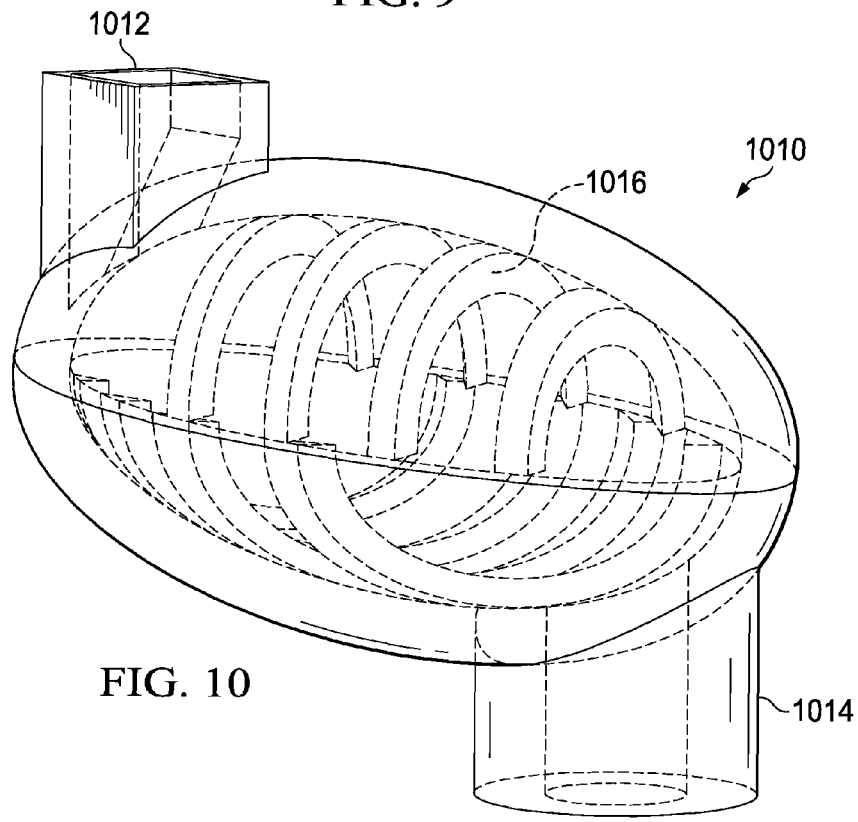
FIG. 10 illustrates an embodiment of a chamber containing a swab when the specimen delivery apparatus housing is in the closed position.

FIG. 10 illustrates the chamber 1010 containing the swab when the specimen delivery apparatus housing is in the closed position. The chamber includes an inlet port 1012 that receives fluid from the bulb or blister pack. The chamber includes an exit port 1014 for the fluid and sample to be carried to the remainder of the fluid transport path. The chamber has grooves, raised thresholds, or other features to direct the fluid. In the illustrated embodiment the features 1016 appear to form a helical or spiral structure.

Figure 11:
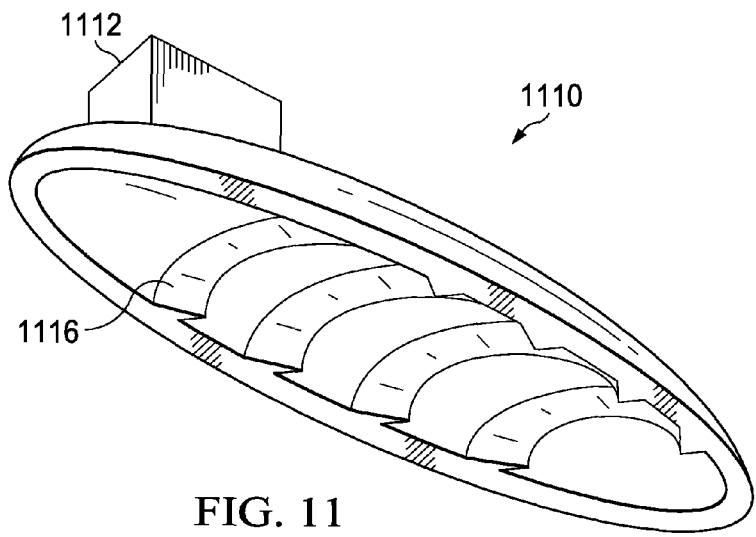
FIG. 11 illustrates an embodiment of the upper portion of the chamber of FIG. 10 with roiling features.
Figure 12:
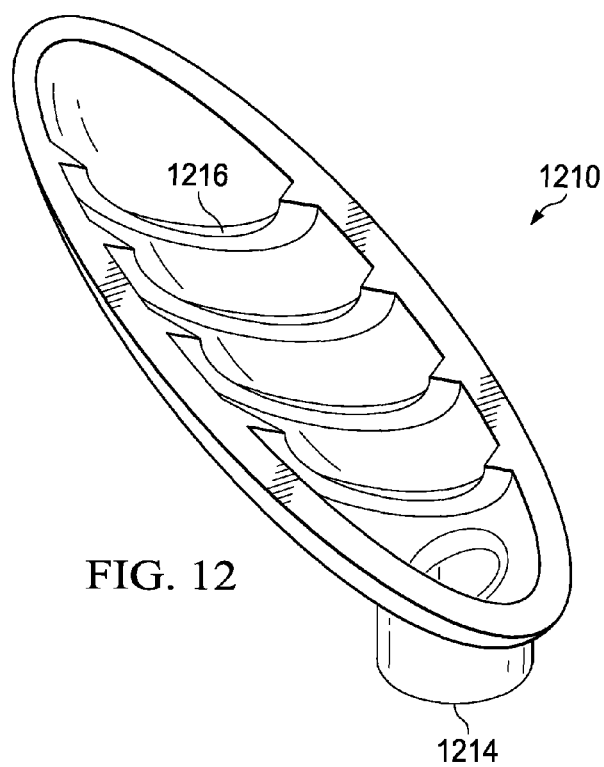
FIG. 12 illustrates an embodiment of the lower portion of the chamber of FIG. 10 with roiling features.

FIG. 11 illustrates one embodiment of the upper portion 1110 of the chamber including the inlet port 1112 and the grooved or raised features 1116 that form a portion of the fluid transport path. FIG. 12 illustrates one embodiment of the lower portion 1210 of the chamber including the exit port 1214 and the grooved or raised features 1216 that form a portion of the fluid transport path. In an embodiment, one or more of the raised features 1216 comprises a chamfered edge, as shown in FIG. 12. The grooved or raised features of the chamber increase the shear forces of the fluid and direct the fluid across the surface of the swab to extract the sample from the swab. The roiling effect caused by these features also enhances mixing of the fluid with the sample.

Figure 13:
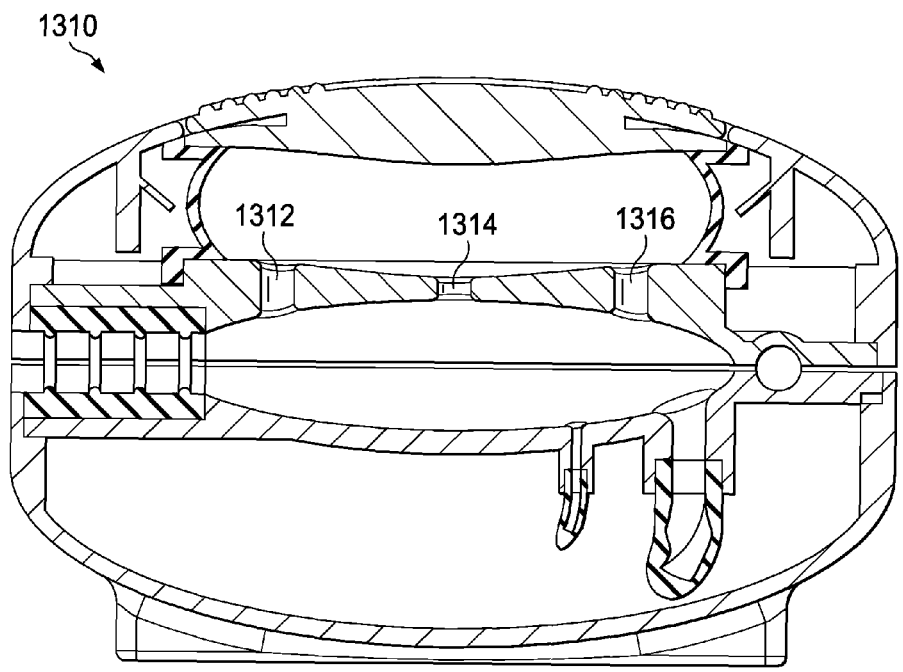
FIG. 13 illustrates an embodiment of a specimen delivery apparatus having multiple entry points for communicating fluid into the chamber.

The housing and midplane may be configured to provide for multiple entry points of fluid into the fluid transport path. FIG. 13 illustrates one embodiment of a specimen delivery apparatus 1310 having multiple entry points 1312, 1314, 1316 for communicating fluid from the bulb or blister pack into the sample chamber.

In one embodiment, the specimen delivery apparatus includes a staging chamber to separate the function of specimen preparation and specimen delivery to the next stage. For example, reagents in the transport fluid may require time beyond the transport time to fully act upon the sample. Electrical, thermal, or acoustic lysis may require time beyond the fluid transport time to complete.

Figure 14:
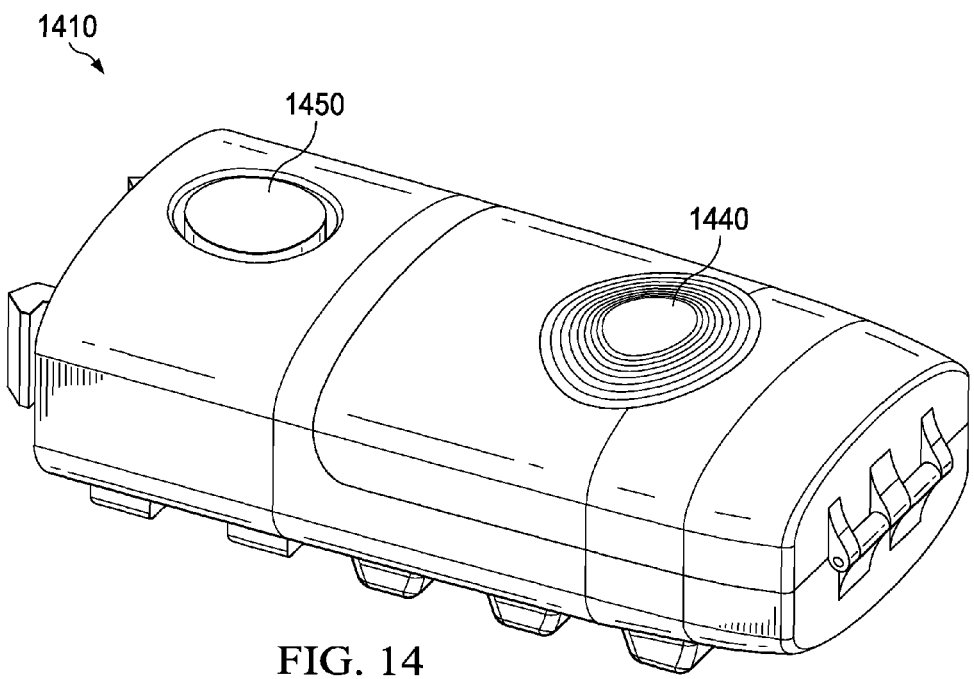
FIG. 14 illustrates an embodiment of a staging or "dual action" specimen delivery apparatus.

FIG. 14 illustrates one embodiment of a staging or "dual action" specimen delivery apparatus 1410. Depressing the first actuator 1440 performs some mixing of the sample with a fluid and transports the fluid with sample to a staging chamber (not shown). A second actuator 1450 propels the prepared specimen to the next stage. The first actuator may be a "bulb" as previously described in one embodiment. The second actuator may be a bulb or any other apparatus for driving the specimen from the chamber to the next stage through the fluid communication port of the specimen delivery apparatus. The first and second actuators are fluid transport actuators.

Figure 15:
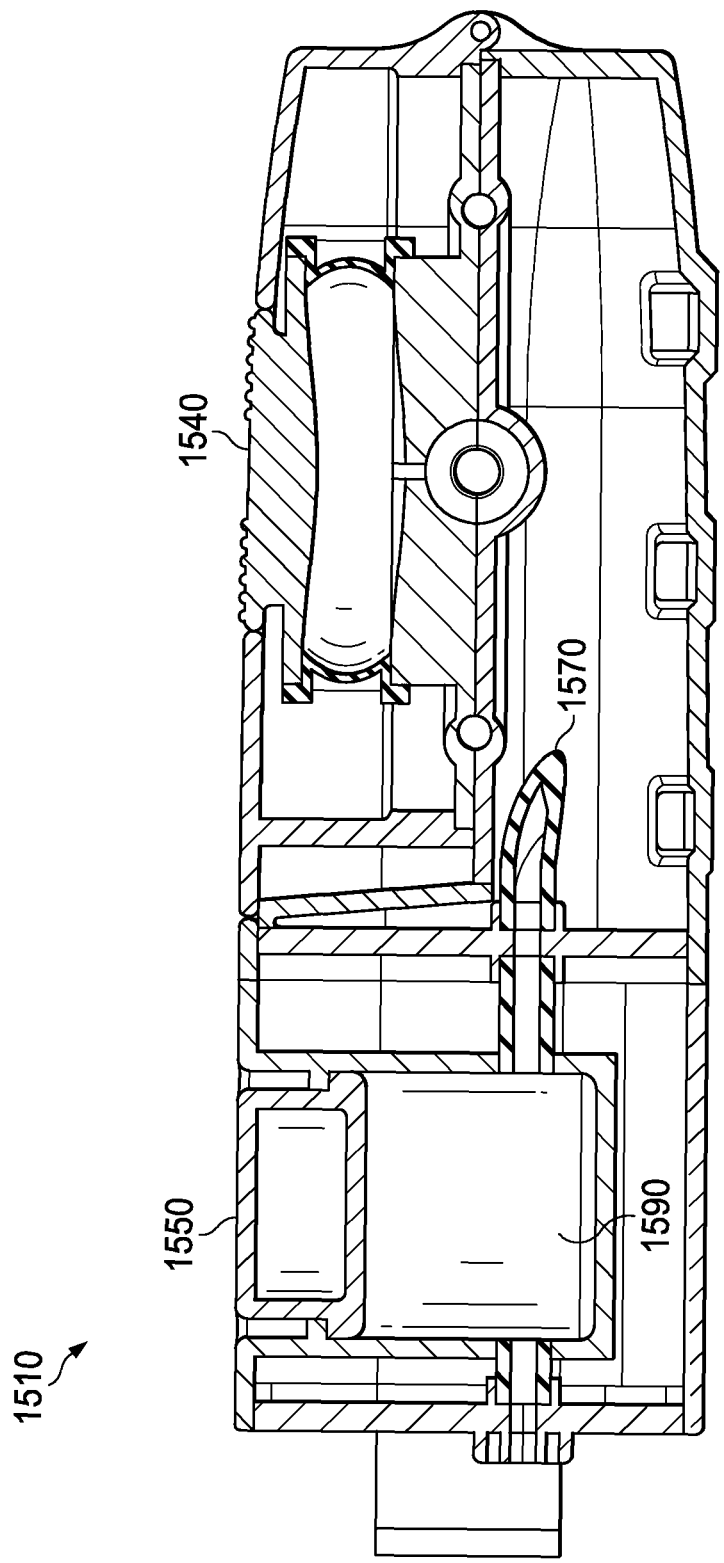
FIG. 15 illustrates a cross-section of an embodiment of the staging or "dual action" specimen delivery apparatus.

FIG. 15 illustrates a cross-section of one embodiment of the staging or dual action specimen delivery apparatus 1510. The first actuator 1540 (such as the previously described first bulb) propels a fluid through the fluid transport path. The propulsion may strip sample from clinical tool (e.g., swab) and otherwise mixes the fluid with the sample. The fluid and sample mixture are transported to the staging chamber 1590 via the fluid transport path which may include channels or fluid transport tubes such as rifled fluid transport tube 1570. When the specimen is ready to be delivered to the next stage of the medical diagnostic system, the user can depress the second actuator 1550. In the illustrated embodiment, the second actuator and staging chamber operate in a manner similar to a syringe to drive the prepared specimen from the staging chamber to the next stage of the medical diagnostic system.

In one embodiment, the next stage of the medical diagnostic system signals when it is ready to accept the specimen (i.e., when the user is cleared to depress the second actuator). In other embodiments, the next stage actively communicates with the specimen delivery apparatus through one or more ports on the backplane to either aid in the preparation of the specimen or to determine or signal when the specimen has been adequately prepared and is ready to be delivered to the next stage of the point-of-care medical diagnostic system.

For example, the staging chamber may be positioned adjacent a transducer for applying at least one of a thermal, mechanical, acoustical, or optical energy to the contents of the staging chamber. A thermal pad, for example, may be used to heat the contents of the staging chamber to a pre-determined temperature. Thermal, mechanical, or acoustical energy may be used for lysis.

The staging chamber may also be equipped with sensors to permit detection of threshold conditions that determine whether the specimen has been prepared appropriately. The sensors also enable controlled application of thermal, mechanical, acoustical, or optical energy to the contents of the staging chamber with the control provided by the next stage of the point-of-care medical diagnostic system. An optical sensor may be used to determine if certain chemical reactions are complete, for example. A thermal sensor may be used to monitor the temperature of the contents of the staging chamber. Power, sensor, and control signals may be communicated between the next stage and the specimen delivery apparatus through electrical ports on the backplane of the specimen delivery apparatus.

In the preceding detailed description, the invention is described with reference to specific exemplary embodiments thereof. A specimen delivery apparatus for in vitro medical diagnostic devices is described. The features of different embodiments disclosed may be combined in order to expand the versatility of the specimen delivery apparatus. Various modifications and changes may be made thereto without departing from the broader scope of the invention as set forth in the claims. The specification and drawings are, accordingly, to be regarded in an illustrative rather than a restrictive sense.

What is claimed is:

1. A specimen delivery apparatus for processing a biological specimen, the specimen delivery apparatus comprising:
   a housing having a first portion and a second portion, wherein the first portion is coupled to the second portion at a hinge, and operable to transition from an open state to a closed state when the second portion is rotated about the hinge toward the first portion;
   an intermediate portion positioned within the housing and having a cavity that forms a portion of a chamber for receiving a sample collector and holding a sample that includes the biological specimen, wherein the chamber is formed by closing the first portion with respect to the second portion, and wherein the intermediate portion and chamber are sealed within the housing in the closed state;
   a fluid transport path fluidly coupled to the cavity and having a roiling feature operable to roil a fluid propelled through the fluid transport path; and
   a first bulb fluidly coupled to the fluid transport path and operable to propel fluid within the apparatus through at least a portion of the fluid transport path that includes the roiling feature when the housing is in a closed state and the first bulb is actuated.

2. The apparatus of claim 1, wherein the housing further comprises an interfacing surface adjacent to the first portion and second portion, and having at least one attachment point for mechanically coupling the specimen delivery apparatus to a second stage apparatus,
   wherein the interfacing surface includes a fluid communication port fluidly coupled to the fluid transport path,
   wherein the interfacing surface further comprises a destructible seal proximate to the fluid communication port, the destructible seal preventing fluid communication through the fluid communication port while the seal is intact,
   wherein actuation of the first bulb communicates the fluid through the fluid communication port when the destructible seal is not intact,
   wherein the fluid communication port of the specimen delivery apparatus is operable to be aligned with a second fluid communication port of the second stage apparatus to enable fluid communication between the specimen delivery apparatus and the second stage apparatus when the specimen delivery apparatus is coupled to the second stage apparatus via the at least one attachment point.

3. The apparatus of claim 1 further comprising a second bulb fluidly coupled to the fluid transportation path, the second bulb being operable to propel fluid along the fluid transportation path when the housing is in the closed state and the second bulb is actuated.

4. The apparatus of claim 1 further comprising an optical port for transmission of light to and from the cavity, the optical port comprising an optically transmissive path through the housing to the cavity.

5. The apparatus of claim 1 wherein the housing comprises an interfacing surface having an electrical port for communication of electricity.

6. The apparatus of claim 5 further comprising a heater positioned within the housing and proximate to the cavity, the heater being electrically coupled to the electrical port and operable to heat the cavity upon the transmission of electrical energy to the electrical port.

7. The apparatus of claim 5 further comprising an acoustic transducer positioned within the housing and proximate to the cavity, the acoustics transducer being electrically coupled to the electrical port and operable to apply acoustic energy to the cavity upon the transmission of electrical energy to the electrical port.

8. The apparatus of claim 5 wherein the electrical port is electrically coupled to the cavity and operable to communicate electrical energy to the cavity.

9. The apparatus of claim 5 further comprising a transducer positioned within the housing and proximate to the cavity, the transducer being coupled to the electrical port and operable to apply at least one of a thermal, mechanical, acoustical, and optical energy to the cavity upon the transmission of electrical energy to the electrical port.

10. The apparatus of claim 9 further comprising a blister pack retainer having a blister pack disposed therein and being disposed along the fluid transportation path upstream from a cavity, the blister pack comprising a fluid that includes at least one of a suspension solution, a reagent, and a solvent.

11. The apparatus of claim 1, wherein the fluid transport path is a first fluid transport path comprising the first bulb, the cavity, and a first fluid transport tube, the apparatus further comprising second fluid transport path in fluid communication with the first fluid transport path, the second fluid transport path having a second fluid transport tube and a cache, wherein the apparatus is operable to direct a portion of the fluid into the cache via the second fluid transport tube upon actuation of the first bulb.

12. The apparatus of claim 1 wherein the housing comprises a retaining feature and the first bulb comprises a latching feature that is operable to engage the retaining feature to retain the first bulb in a compressed state when the first bulb is actuated.

13. The apparatus of claim 1 wherein the roiling feature comprises grooves, and wherein the grooves form a helical or spiral structure within the cavity.

14. The apparatus of claim 13 wherein the fluid transport path comprises a rifled fluid transport tube.

15. The apparatus of claim 1, wherein the roiling feature comprises at least one raised feature disposed within the cavity, the raised feature having a chamfered edge.

16. The apparatus of claim 1, further comprising:
a staging chamber fluidly coupled to the cavity by a fluid transport tube;
wherein the first bulb is operable to propel fluid through the cavity and the fluid transport tube to the staging chamber when the housing is in a closed state and the first bulb is actuated; and
wherein the apparatus further comprises a second actuator operable to propel fluid from the staging chamber.

17. The apparatus of claim 16, further comprising a transducer proximate to the staging chamber and operable to transmit at least one of a thermal, mechanical, acoustical, and optical energy to the staging chamber.

18. The apparatus of claim 1, wherein the cavity comprises a chamber for receiving at least a portion of a sample collector.

19. The apparatus of claim 18, wherein the sample collector is a swab, and wherein the intermediate portion comprises a swab shaft seal.

20. A method of preparing a biological sample for analysis, the method comprising:
receiving a sample collector within a cavity of a specimen delivery apparatus, the sample collector comprising a biological sample, wherein the specimen delivery apparatus comprises:
a housing having a first portion and a second portion, wherein the first portion is coupled to the second portion at a hinge, and operable to transition from an open state to a closed state when the second portions rotated about the hinge toward the first portion;
an intermediate portion positioned within the housing and comprising the cavity, wherein the intermediate portion is sealed within the housing between the first portion and a second portion and the cavity forms a portion of an enclosed chamber when the housing is transitioned to the closed state, the cavity comprising a portion of a fluid transport path having a roiling feature that is operable to roil fluid propelled through the fluid transport path; and
a first bulb fluidly coupled to the fluid transport path and operable to propel fluid within the apparatus through at least a portion of the fluid transport path that includes the roiling feature when the housing is in a closed state and the first bulb is actuated,
wherein the method further comprises depressing the first bulb to roil a fluid across the sample collector.

21. The method of claim 20, further comprising mechanically coupling the specimen delivery apparatus to a second-stage apparatus at an attachment point of the specimen delivery apparatus.

22. The method of claim 21, wherein the specimen delivery apparatus further comprises an interfacing surface having at least one fluid communication port and a destructible seal preventing fluid communication through the fluid communication port while the seal is intact, the method further comprising fracturing the destructible seal and communicating the fluid through the fluid communication port to the second-stage apparatus.

23. The method of claim 20, wherein the specimen delivery apparatus further comprises an optical port for transmission of optical energy to and from the cavity, the method further comprising directing optical energy to the biological sample via the optical port.

24. The method of claim 20, wherein the specimen delivery apparatus further comprises an electrical port for communication of electrical power and a transducer coupled to the electrical port for applying at least one of a thermal, mechanical, acoustical, and optical energy to the sample upon the application of power to the electrical port, the method further comprising activating the transducer to apply at least one of thermal, mechanical, acoustical, and optical energy to the sample.

25. The method of claim 20, further comprising adding the fluid to the biological sample, the fluid comprising at least one of a suspension solution, a reagent, and a solvent.

26. The method of claim 25, further comprising directing at least a portion of the fluid that includes at least a portion of the biological sample to a cache of the specimen delivery apparatus.

* * * * *

UNITED STATES PATENT AND TRADEMARK OFFICE
CERTIFICATE OF CORRECTION

PATENT NO.         : 9,475,042 B2                                              Page 1 of 1
APPLICATION NO.    : 14/920516
DATED              : October 25, 2016
INVENTOR(S)        : Carrano et al.

It is certified that error appears in the above-identified patent and that said Letters Patent is hereby corrected as shown below:

In the claims

- Column 10, Claim 7, Line 3: Replace "acoustics" with -- acoustic --;
- Column 11, Claim 11, Line 4: insert -- a -- in comprising a second fluid; and
- Column 12, Claim 20, Line 4: Replace "portions" with -- portion is --.

Signed and Sealed this
Twentieth Day of December, 2016

Michelle K. Lee
*Director of the United States Patent and Trademark Office*